United States Patent [19]

Miller et al.

[11] Patent Number: 4,804,499

[45] Date of Patent: Feb. 14, 1989

[54] PROCESS FOR THE PREPARATION OF N-SUBSTITUTED AMINOMETHYLPHOSPHONIC ACIDS

[75] Inventors: William H. Miller, Glendale; David B. Reitz; Mitchell J. Pulwer, both of St. Louis, all of Mo.

[73] Assignee: Monsanto Company, St. Louis, Mo.

[21] Appl. No.: 778,958

[22] Filed: Sep. 23, 1985

[51] Int. Cl.$^4$ ............................................. C07F 9/38
[52] U.S. Cl. ....................... 260/502.5 F; 260/502.5 D
[58] Field of Search ................................. 260/502.5 F

[56] References Cited

U.S. PATENT DOCUMENTS

| | | | |
|---|---|---|---|
| 3,288,846 | 11/1966 | Irani | 260/500 |
| 3,567,768 | 3/1971 | Shen | 260/502.5 |
| 3,927,080 | 12/1975 | Gaertner | 260/502.5 |
| 4,009,204 | 2/1977 | Krueger et al. | 260/502.5 |
| 4,065,491 | 12/1977 | Pfiegel et al. | 260/502.5 |
| 4,140,791 | 2/1979 | Chen | 424/260 |
| 4,237,065 | 12/1980 | Ehrat | 260/502.5 |
| 4,400,330 | 8/1983 | Wong et al. | 260/502.5 |
| 4,442,041 | 4/1984 | Subramanian | 260/502.5 F |
| 4,578,224 | 3/1986 | Bayer et al. | 260/502.5 F |

FOREIGN PATENT DOCUMENTS 0055695 12/1981 European Pat. Off..
47-112 1/1972 Japan.

OTHER PUBLICATIONS

Wagner et al, "Synthetic Organic Chemistry" (1953), pp. 678 and 679.
Sut et al, "N-Monoalkylation of Some 2-Oxo and 2,5-Diketopiperazines", *Chimie Therapeutique*, 4(3), 167-173 (1969).
Okawara et al, "Convenient Syntheses of Piperazines-2,5-Diones and Lactams from Halocarboxamides Using Phase Transfer Catalysts", *Chemistry Letters*, 1981, pp. 185-188.
Cavicchioni et al, "Base-promoted Reactions of α-Halogenoalkylanilides", *J. Chem. Soc. Perkin Trans.* I, pp. 2969-2972 (1982).

*Primary Examiner*—J. E. Evans
*Attorney, Agent, or Firm*—Frank D. Shearin

[57] ABSTRACT

A process for the preparation of an N-substituted aminomethylphosphonic acid comprising reacting a 2,5-diketopiperazine compound with phosphorous acid and formaldehyde in an acidic medium.

8 Claims, No Drawings

PROCESS FOR THE PREPARATION OF N-SUBSTITUTED AMINOMETHYLPHOSPHONIC ACIDS

BACKGROUND OF THE INVENTION

This invention relates to the synthesis of N-substituted aminomethylphosphonic acids and more particularly to an improved process in which an N-substituted 2,5-diketopiperazine is reacted with phosphorous acid and formaldehyde in an acidic medium to produce an N-substituted aminomethylphosphonic acid.

N-substituted aminomethylphosphonic acids are useful intermediates in the preparation of various products, including sequestering agents and herbicides. Thus, for example, an N-alkyl-N-phosphonomethylamino acid, such as N-isopropyl-N-phosphonomethylglycine, can be dealkylated under alkaline conditions to the corresponding N-phosphonomethylamino acid using the method of the copending and coassigned application of Miller and Balthazor, Ser. No. 687,404 filed Dec. 28, 1984, now abandoned.

N-phosphonomethylglycine, known also by its common name glyphosate, is a highly effective and commercially important phytotoxicant useful in controlling a large variety of weeds. It is applied to the foliage of a very broad spectrum of annual and perennial grasses and broadleaf plants. Industrial uses include control of weeds along roadsides, waterways, transmission lines and in storage areas and other non-agricultural areas. Usually glyphosate is formulated into herbicidal compositions in the form of its various salts in solution, preferably water.

Because of its commercial importance, many processes for making glyphosate have been published. Processes are also known for the preparation of other phosphonomethylated amine compounds. In the former category, for example, is Gaertner U.S. Pat. No. 3,927,080 which describes the preparation of N-t-butyl-N-phosphonomethylglycine by reacting t-butylamine with a bromoacetate ester to produce an ester of N-t-butyl-glycine, and thereafter reacting the N-t-butylglycine ester with formaldehyde and dialkyl phosphite to produce esters of N-t-butyl-N-phosphonomethylglycine. The latter product is hydrolyzed under acidic conditions to produce glyphosate.

European Pat. No. 00 55 695 discloses a process for splitting a 1-arylmethyl group from an N-1-arylalkyl-N-phosphonomethylglycine by hydrogenolytic cleavage. The glyphosate precursor is prepared by reaction of an N-1-arylalkylglycine with phosphorous acid and formaldehyde in an aqueous hydrochloric acid medium.

Pfliegel et al U.S. Pat. No. 4,065,491 describes the preparation of glyphosate directly by condensation of glycine, formaldehyde, and a dialkyl phosphite in an aqueous alkaline medium comprising sodium hydroxide.

Ehrat U.S. Pat. No. 4,237,065 describes a synthesis substantially similar to that disclosed in Pfliegel et al. However, Ehrat carries out the reaction using a tertiary amine base in an alcohol medium rather than the sodium hydroxide solution utilized by Pfliegel et al.

Irani and Moedritzer U.S. Pat. No. 3,288,846 also describes the reaction of other nitrogen compounds such as ammonia, or a primary or secondary amine, with an aldehyde or ketone and phosphorous acid to form an aminoalkylenephosphonic acid. However, unlike the processes disclosed by Pfliegel et al and Ehrat, the Irani process is carried out in an aqueous medium having a pH below about 4.

Shin et al U.S. Pat. No. 3,567,768 describes the preparation of an aminoalkylenephosphonic acid compound by reaction of a reactive nitrogenous material (i.e., a nitrogen containing or nitrogenous compound such as ammonia, a primary amine, or secondary amine), an aldehyde or ketone, and an excess of phosphorous acid. Where the nitrogenous reactant is ammonia or an ammonium salt, the product is the same as that prepared in accordance with the Krueger patent, discussed below. The exemplary disclosure of Shin describes a preparation in which phosphorous acid is premixed with ammonium chloride and water, and the resultant mixture is heated to reflux while formaldehyde is added thereto.

Japanese patent Sho 47[1972]-112 describes a method for the treatment of cellulose fibers with a solution which is prepared by the reaction of a nitrogen compound, phosphorous acid, and formalin. The nitrogen compound is one which contains two or more amino groups, such as for example, urea, thiourea, guanidine, or an alkyldiamide. However, the reference is concerned with enhancing the characteristics of the treated fiber and contains no disclosure of the structure of any product that may be formed by reaction of the aforesaid materials. Nor does the reference report any analytical work which might provide an indication of the structure of such product.

Krueger et al U.S. Pat. No. 4,009,204 describes the preparation of nitrilo tris(methylenephosphonic acid) by reaction of an aliphatic amide with formaldehyde and a phosphorous trihalide. In the Krueger process, the amide substrate is preferably premixed with the aldehyde and the phosphorus trihalide added dropwise thereto. Alternatively, the aldehyde and phosphorus trihalide are premixed, and the acid amide slowly added to the latter premixture.

A variety of 1,4-disubstituted 2,5-diketopiperazines are known to the art and are recognized to be useful for various purposes. Thus, for example, Chan et al U.S. Pat. No. 4,140,791 discloses the use of 1-4-di(2,6-dimethylphenyl)-2,5-diketopiperazine for control of various fungal diseases. Sut et al "N-Monoalkylation of Some 2-Oxo and 2,5-Dioxopiperazines" *Chimie Therapeutique*, Vol. 4 (3) pgs. 167-173 (1969), describes the synthesis of a series of 2-oxopiperazines and 2,5-dioxopiperazines which were found to have analgesic and anesthetic activities. Among the specific compounds disclosed by Sut et al are 2,5-diketopiperazines and 3-substituted 2,5-diketopiperazines which are mono- or dialkylated in an N-position, or N,N'-positions, with ethyl, benzyl, hydroxyethyl or acetoxyethyl. Other references contain specific disclosure of 1,4-dimethyl-2,5-diketopiperazine, 1,4-diethyl-2,5-diketopiperazine, 1,4-diphenyl-2,5-diketopiperazine, and 1,4-dibenzyl-2,5-diketopiperazine. However, it is believed that none of these references disclose the use of any such compounds in the preparation of any N-substituted aminomethylphosphonic acid.

Okawara et al "Convenient Syntheses of Piperazine-2,5-diones and Lactams from Halocarboxamides Using Phase Transfer Catalysts" *Chemistry Letters*, 1981, pgs. 185-189, shows the syntheses of various 1,4-disubstituted-2,5-diketopiperazines. Among the compounds whose syntheses are reported in Okawara et al are 1,4-dibenzylpiperazine-2,5-dione, 1,4-diphenylpiperazine-2,5-dione and 1,4-diphenyl-3,6-dimethylpiperazine-2,5- dione. The reference does not report any use for the products synthesized.

Cavicchioni et al "Base Promoted Reactions of α-Halogenoalkylanilides", *J. Chem. Soc., Perkin Trans. I*, pgs. 2969–2972 (1982), reports the preparation of both N-N'-dialkyldiketopiperazines and 2-amino-2-haloalkyloxazolidones by intermolecular condensations of the same reactants used in the synthesis described by Okawara et al. Cavicchioni et al do not give much detail on the reaction system utilized and do not describe any uses for the N-N'-dialkylpiperazines obtained.

Wong et al U.S. Pat. No. 4,400,330 describes the preparation of bis(phosphonomethyl)-2,5-diketopiperazine by phosphonomethylation of 2,5-diketopiperazine, followed by isolation of the bis(phosphonomethyl)-2,5-diketopiperazine and alkaline hydrolysis thereof to produce the trisodium salt of glyphosate. In the phosphonomethylation reaction, formaldehyde and glacial acetic acid are added to 2,5-diketopiperazine to produce a suspension which is refluxed. Thereafter, phosphorus trichloride is added to the reaction mixture which is then maintained at reflux until all hydrogen chloride byproduct has been driven off. After additional refluxing of the reaction slurry, the product is dried in vacuo, dissolved in water, and treated sequentially with caustic solution and then mineral acid to effect hydrolysis and produce glyphosate.

The co-pending and co-assigned application of Miller and Taylor, Ser. No. 778,818 filed 9-23-85 describes the novel compound 1,4-diisopropyl-2,5-diketopiperazine and its use in the preparation of N-isopropylglycine. The disclosure of the co-pending application further describes the phosphonomethylation of N-isopropylglycine to N-isopropylglyphosate and conversion of the latter intermediate to glyphosate by dealkylation in an alkaline medium in accordance with the disclosure of Miller and Balthazor, Ser. No. 687,404 filed Dec. 28, 1984.

The co-pending, co-assigned application of Miller and Taylor Ser. No. 778,817 filed 9-23-85 describes novel processes for the preparation of various 1,4-disubstituted-2,5-diketopiperazines and the conversion of the latter to glyphosate via the N-substituted glycine derivatives. Certain of the subject matter disclosed therein relates to the present invention.

SUMMARY OF THE INVENTION

Among the several objects of the present invention, therefore, may be noted the provision of an improved process for the preparation of N-substituted aminomethylphosphonic acid compounds; the provision of such a process which can be carried out without isolation of intermediates; the provision of such a process which produces a product suitable for conversion to glyphosate or glyphosate derivatives, for example, by the process of Miller et al Ser. No. 687,404 filed Dec. 28, 1984, and the provision of a process by which N-substituted aminomethylphosphonic acid compounds may be prepared from 2,5-diketopiperazines of the type whose preparation is described in the co-pending and co-assigned application of Ser. No. 778,818 filed 9-23-85 and Ser. No. 778,817 filed 9-23-85.

Briefly, therefore, the present invention is directed to a novel process for the preparation of an N-substituted aminomethylphosphonic acid comprising reacting a 2,5-diketopiperazine compound with phosphorous acid and formaldehyde in an acidic medium, said diketopiperazine compound represented by the formula

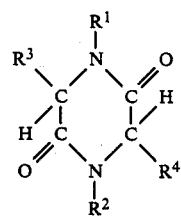

wherein $R^1$ and $R^2$ are independently selected from among hydrogen, alkyl, aryl, arylalkyl, and carboxylalkyl, and $R^3$ and $R^4$ are independently selected from among hydrogen, alkyl and aryl. The product can be represented by the formula

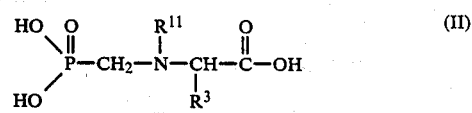

provided that $R^3$ and $R^4$ are identical, and either $R^1$ and $R^2$ are identical, both $R^1$ and $R^2$ are hydrolyzable under the reaction conditions, or one of $R^1$ and $R^2$ is hydrogen and the other is hydrolyzable under the reaction conditions. Otherwise the product comprises a mixture comprising

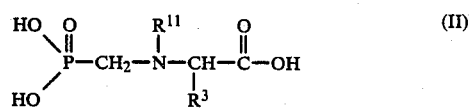

and

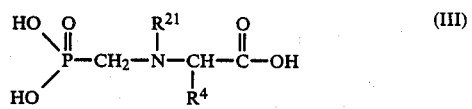

In formulae II and III, $R^{11}$ is selected from among hydrogen and phosphonomethyl when $R^1$ is either hydrogen or a group hydrolyzable under the reaction conditions, $R^{11}$ otherwise being identical to $R^1$. $R^{21}$ is selected from among hydrogen and phosphonomethyl when $R^2$ is either hydrogen or a group hydrolyzable under the reaction conditions, $R^{21}$ otherwise being identical to $R^2$.

Other objects and features will be in part apparent and in part pointed out hereinafter.

DESCRIPTION OF THE PREFERRED EMBODIMENT

In accordance with the invention, a novel process has been discovered by which an N-substituted 2,5-diketopiperazine compound can be directly phosphonomethylated to produce an N-substituted aminomethylphosphonic acid, without the necessity of isolating any intermediate product. Reaction of the substituted diketopiperazine substrate with formaldehyde and phosphorous acid in an acidic medium produces the desired products, phosphonomethylated amino acids.

Generally, the substrate utilized in the process of the invention can be represented by the structural formula

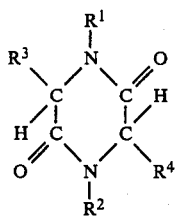

In this structure, $R^1$ and $R^2$ are independently selected from among hydrogen, alkyl, aryl, arylalkyl, and carboxyalkyl. Preferably, the substituents comprising $R^1$ and $R^2$ may contain up to about 8 carbon atoms. Among the alkyl groups which may comprise $R^1$ and/or $R^2$ are methyl, ethyl, n-propyl, isopropyl, n-butyl, secondary butyl, tertiary butyl, octyl, cyclohexyl, ethylcyclopentyl, and the like. Among the aryl groups which may constitute $R^1$ and/or $R^2$ are phenyl, tolyl, dimethylphenyl, and the like. Suitable arylalkyl groups include benzyl, 1-phenylethyl 2-napthylmethyl, methylphenylmethyl and the like. The carboxyalkyl groups which may comprise $R^1$ and/or $R^2$ include, for example, carboxymethyl, carboxyethyl, carboxypropyl, carboxybutyl, carboxypentyl, and carboxyheptyl.

Substituents $R^3$ and $R^4$ in the substrate compound are selected from among hydrogen, alkyl and aryl. Where $R^3$ or $R^4$ is an alkyl, aryl or carboxyalkyl group, it may typically comprise any of the alkyl, aryl or carboxyalkyl groups which may comprise $R^1$ and/or $R^2$ as listed above.

In carrying out the process of the invention, it is preferred that the substrate be initially dissolved or dispersed in an aqueous acidic medium such as, for example, hydrochloric acid, hydrobromic acid or sulfuric acid, the acid typically having a strength of 10% to 25% by weight. Hydrochloric acid at a strength of between about 15% and about 25% by weight is a particularly effective medium for carrying out the reaction. After the substrate has been dissolved or dispersed in the aqueous acidic medium, the resultant mixture is preferably heated, for example, to a temperature of 70°-120° C. to effect hydrolytic cleavage of the ring at the two amide bonds. Advantageously, the system may be heated to reflux temperature, which in the case of 20% hydrochloric acid is typically in the range of 105°-110° C. In the acidic medium the reaction with phosphorous acid and formaldehyde may be carried out to produce the above described products without isolation of any intermediate.

The process may be initiated by heating a mixture of substrate and phosphorous acid in a hydrochloric, hydrobromic or sulfuric acid medium. In an alternative procedure the substrate may be mixed with a phosphorus trihalide, such as phosphorus trichloride or phosphorus tribromide, and water, the phosphorus trihalide reacting with the water to produce a mixture of phosphorous acid and either hydrochloric or hydrobromic acid. Whenever and in whatever form it is introduced into the reaction system, phosphorous acid should be charged in a stoichiometric proportion of at least two moles per mole of substrate. Preferably, about a 10% excess of phosphorous acid is charged.

With the phosphorous acid incorporated in the mixture, the temperature of the system is maintained at at least about 90° C., preferably at just below reflux, while formaldehyde is added slowly thereto. The formaldehyde may be added in any of its various monomeric or oligomeric forms, but is most conveniently added as formalin. Typically, the addition of formaldehyde may be carried out over a period of at least 0.5 hour, after which the temperature is preferably maintained at reflux for at least 2 hours. Formaldehyde should be added in a stoichiometric proportion of at least two moles per mole of substrate. Complete conversion of the substrate is promoted by introducing an approximately 20% excess of formaldehyde into the reaction zone.

Provided that $R^3$ and $R^4$ are identical, and either $R^1$ and $R^2$ are identical, both $R^1$ and $R^2$ are hydrolyzable under the reaction conditions, or one of $R^1$ and $R^2$ is hydrogen and the other is hydrolyzable under the reaction conditions, the product of the reaction corresponds to the formula

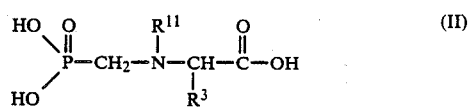

Otherwise the product comprises a mixture comprising

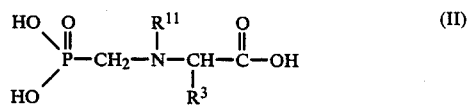

and

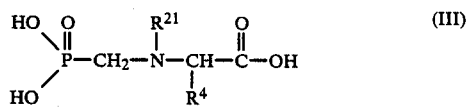

In each of the above formulae II and III, $R^{11}$ is selected from among hydrogen and phosphonomethyl when $R^1$ is either hydrogen or group hydrolyzable under the reaction conditions. Otherwise $R^{11}$ is identical to $R^1$. $R^{21}$ is selected from among hydrogen and phosphonomethyl when $R^2$ is either hydrogen or a group hydrolyzable under the reaction conditions, $R^{21}$ being otherwise identical to $R^2$. In the context of this disclosure "not subject to hydrolysis" or "not hydrolyzable" more precisely means that the group in question is not subject to hydrolytic cleavage from the amine nitrogen in the reaction product.

In the case where $R^1$ or $R^2$ is hydrogen or a hydrolytically cleavable group, the extent of phosphonomethylation is dependent on the reactant ratios and the reaction conditions. Using less than two moles of phosphorous acid and less than two moles of formaldehyde per mole of substrate, the monophosphonomethylated product may predominate. By increasing the relative proportions of phosphorous acid and formaldehyde to substrate substantially above the preferred ratios, the formation of bisphosphonomethylated product is favored.

After the reaction is completed, the product may be recovered if desired by conventional techniques such as, for example, crystallization. However, where the N-substituted aminomethylphosphonic acid product is prepared as an intermediate for glyphosate, conversion to glyphosate can be carried out directly without recovery of intermediate from the phosphonomethylation reaction medium.

Where the process of the invention is used in the synthesis of glyphosate, $R^3$ and $R^4$ should both be hydrogen and $R^1$ and $R^2$ are preferably alkyl substituents. Most preferably, both $R^1$ and $R^2$ are isopropyl. In such instance the product of the reaction is N-isopropyl-N-phosphonomethylglycine, which is converted in very high yield to glyphosate in accordance with the alkaline medium dealkylation process described in the aforesaid application of Miller et al, Ser. No. 687,404 filed Dec. 28, 1984.

The following examples illustrate the invention.

EXAMPLE 1

A 100 ml 3-necked flask was equipped with a magnetic stir bar, thermometer, condenser and an addition funnel. To this flask were added 1,4-diisopropyl-2,5-diketopiperazine (1.98 g; 10.0 mmol), water (25 ml), concentrated hydrochloric acid (10 ml), and phosphorous acid (1.72 g; 21 mmol). The resulting mixture was heated rapidly to 105° C. At this point, a solution of 37% formaldehyde in water (1.95 g; 24 mmol) was added slowly drop-wise to the mixture. Upon completion of the addition of formaldehyde, the reaction mixture was heated at 104°–105° C. for 17 hours. Analysis of the reaction mixture by HPLC indicated the presence of 1.49 g (70.7% yield) of N-isopropyl-N-phosphonomethylglycine.

EXAMPLE 2

Utilizing the procedure described in Example 1, 1,4-dimethyl-2,5-diketopiperazine (1.42 g; 10.0 mmol) was converted to N-methyl-N-phosphonomethylglycine. HPLC analysis indicated a yield of 97%. Upon isolation of the product by ion exchange chromatography, a yield of 2.93 g (80%) of the product was obtained.

EXAMPLE 3

Using the procedure described in Example 1, 1,4-dibenzyl-2,5-diketopiperazine (2.94 g; 10.0 mmol) was converted to N-benzyl-N-phosphonomethylglycine. After isolation by ion exchange chromatography, a yield of 1.83 g (35.3%) of product was obtained. In this reaction 50% of the starting 1,4-dibenzyl-2,5-diketopiperazine was recovered unchanged.

EXAMPLE 4

To a 3-necked round-bottom flask equipped with a stir bar, thermometer, reflux condenser and addition funnel, were added 2,5-diketopiperazine (114 g; 1.0 mol), phosphorous acid (16.4 g; 0.20 mol) concentrated hydrochloric acid (300 ml) and water (200 ml). The resulting mixture was stirred and heated to 110° C. At that point formaldehyde solution (16.2 g of a 37% aqueous solution, 0.2 mol) was added drop-wise to the mixture over a period of 30 minutes. During addition of the formaldehyde and for an additional period of 72 hours thereafter, the temperature was maintained at approximately 110° C. Upon cooling, the solution was analyzed for N-phosphonomethylglycine by HPLC. The yield of N-phosphonomethylglycine was 52% (basis formaldehyde).

In view of the above, it will be seen that the several objects of the invention are achieved and other advantageous results attained.

As various changes could be made in the above methods without departing from the scope of the invention, it is intended that all matter contained in the above description or shown in the accompanying drawings shall be interpreted as illustrative and not in a limiting sense.

What is claimed is:

1. A process for the preparation of an N-substituted aminomethylphosphonic acid comprising reacting a 2,5-diketopiperazine compound with phosphorous acid and formaldehyde in an acidic medium, said diketopiperazine compound represented by the formula:

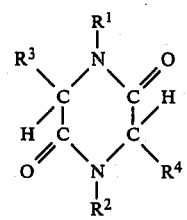

wherein $R^1$, $R^2$, $R^3$, and $R^4$ are independently selected from the group consisting of hydrogen, alkyl, aryl, arylalkyl, and carboxylalkyl, the product represented by the formula:

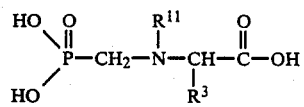

provided that $R^3$ and $R^4$ are identical, and either $R^1$ and $R^2$ are identical, both $R^1$ and $R^2$ are hydrolyzable under the reaction conditions, or one of $R^1$ and $R^2$ is hydrogen and the other is hydrolyzable under the reaction conditions, the product otherwise comprising a mixture comprising

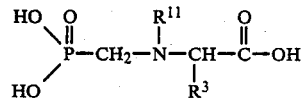

and

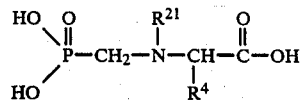

$R^{11}$ being selected from the group consisting of hydrogen and phosphonomethyl when $R^1$ is either hydrogen or a group hydrolyzable under the reaction conditions, $R^{11}$ otherwise being identical to $R^1$, $R^{21}$ being selected from the group consisting of hydrogen and phosphonomethyl when $R^2$ is either hydrogen or a group hydrolyzable under the reaction conditions, $R^{21}$ being otherwise identical to $R^2$.

2. A process as set forth in claim 1 wherein $R^1$ and $R^2$ are the same, and $R^3$ and $R^4$ are hydrogen.

3. A process as set forth in claim 2 wherein $R^1$ and $R^2$ are selected from the group consisting of benzyl, carboxymethyl, isopropyl and hydrogen.

4. A process as set forth in claim 3 wherein $R^1$ and $R^2$ are isopropyl.

5. A process as set forth in claim 4 further comprising dealkylating the N-isopropyl-N-phosphonomethylglycine product in the presence of a base to produce a salt of glyphosate.

6. A process as set forth in claim 1 wherein said diketopiperazine is introduced into an aqueous medium comprising an acid selected from the group consisting of sulfuric acid, hydrochloric acid, and hydrobromic acid, and thereafter formaldehyde is added to said medium in the presence of phosphorous acid to effect the phosphonomethylation.

7. A process as set forth in claim 6 wherein a mixture is prepared comprising said acidic aqueous medium, said diketopiperazine, and phosphorous acid, said mixture is heated at a temperature of between about 70° and about 120° C., and thereafter formaldehyde is added slowly to the mixture while the temperature of the mixture is maintained at least about 90° C.

8. A process as set forth in claim 7 wherein said mixture is maintained at a temperature of approximately atmospheric reflux temperature during the addition of formaldehyde.

* * * * *